United States Patent [19]

Shinoki et al.

[11] Patent Number: 5,190,726
[45] Date of Patent: Mar. 2, 1993

[54] APPARATUS FOR MEASURING THE FLOW RATE OF WATER VAPOR IN A PROCESS GAS INCLUDING STEAM

[75] Inventors: Toshio Shinoki; Akira Sasaki; Shuichi Matsumoto, all of Amagasaki, Japan

[73] Assignee: Mitsubishi Denki Kabushiki Kaisha, Tokyo, Japan

[21] Appl. No.: 666,907

[22] Filed: Mar. 11, 1991

[30] Foreign Application Priority Data

Mar. 13, 1990 [JP] Japan .................................. 2-63055

[51] Int. Cl.$^5$ .................................. G01N 25/66
[52] U.S. Cl. .................................. 422/62; 422/111; 73/861.04; 429/22
[58] Field of Search ............... 422/62, 111; 73/861.04; 374/16, 18–20, 25, 27, 28; 429/17, 19, 22; 436/40; 208/DIG. 1

[56] References Cited

U.S. PATENT DOCUMENTS

| | | | |
|---|---|---|---|
| 3,585,078 | 6/1971 | Sederquist | 429/17 |
| 3,898,882 | 8/1975 | Prokopius | 73/861.04 |
| 3,961,986 | 6/1976 | Waldman | 429/17 |
| 4,722,873 | 2/1988 | Matsumura | 429/17 |
| 4,759,637 | 7/1988 | Baillie | 374/27 |
| 4,843,867 | 7/1989 | Cummings | 422/111 |
| 4,946,288 | 8/1990 | Siska et al. | 374/20 |

OTHER PUBLICATIONS

MBW Dew-point Measuring Instrument DP4-D-B/C, Oct. 1985 "Process Keisoku Seigyo Binnran", Nikkan Kogyo Shinbunsha, Nov. 25, 1970.

Primary Examiner—James C. Housel
Assistant Examiner—Jan M. Ludlow
Attorney, Agent, or Firm—Leydig, Voit & Mayer

[57] ABSTRACT

An apparatus for measuring the flow rate of water vapor in a process gas including steam includes a sample system having a dew point meter and a pressure meter, and an inert gas supply device for mixing an inert gas with a process gas in the sample system. The process gas comprises a first gas, such as natural gas, and steam. A partial pressure calculating unit calculates the partial pressure of the water vapor contained in the gas mixture on the basis of the dew point of the mixture measured by the dew point meter and the pressure measured by the pressure meter. A flow rate calculating unit calculates the flow rate of the steam contained in the process gas on the basis of the water vapor partial pressure, the inert gas flow rate, and the flow rate of the first gas in the process gas.

6 Claims, 2 Drawing Sheets

APPARATUS FOR MEASURING THE FLOW RATE OF WATER VAPOR IN A PROCESS GAS INCLUDING STEAM

BACKGROUND OF THE INVENTION

1. Field of the Invention

The present invention relates to an apparatus for measuring the flow rate of water vapor in a process gas including steam and, more specifically, to an apparatus which is capable of measuring, with a high level of precision, the flow rate of the steam contained in a gas with a high dew point supplied to, a process reactor such as a fuel cell power generating system when the power generating system is being operated, adjusted or checked.

2. Description of the Related Art

FIG. 2 is a schematic diagram for explaining the principles of a conventional method of measuring a dew point by means of a thermoelectrically cooled, photoelectric dew point meter, the method being known from, e.g., "Handbook of Process Measurement and Control" (FIG. 3.324, published in 1970 by Nikkan Kogyo Shinbun). As shown in FIG. 2, a photoelectric dew point meter for use in process control has a dew point detecting section 10 into which a sample gas is drawn by suction. A mirror 3 made of a metal is disposed inside the section 10. The temperature of the mirror 3, which is automatically held at the dew point of the gas, is continuously measured to indicate the dew point, and the measured dew point is used to perform automatic control. The mirror 3 is cooled by a thermoelectric cooling device 4 employing the Peltier effect and comprising semi-conductor cooling elements. The cooling and the heating of the device 4 are controlled in such a manner as to maintain the temperature of the mirror 3 at the dew point. Specifically, when the humidity of the gas flowing into section 10 changes, the amount of dew on the surface of the mirror 3 increases or decreases. This increase or decrease causes a corresponding increase or decrease in the quantity of light projected from a lamp 1 through a slit 2. This light is then reflected from the mirror 3 and then enters a cadmium sulfide member 6. On the basis of the change in the light quantity, a mirror surface temperature control section 11 comprising an adjuster 8 and a controller 9 operates to either raise or lower the temperature of the mirror 3 so that whenever the dew point changes, the temperature of the mirror 3 is updated to become equal to the new dew point. The temperature of the mirror 3, which is thus held at the dew point, is indicated by a thermometer 5. On the basis of the indicated dew point and on the basis of a certain relation between a gas temperature and saturated water vapor pressure, shown in the following Table 1 (which is the same as Table 3.53 shown in the above-mentioned document), the partial pressure of the water vapor is obtained.

TABLE 1

| SATURATED WATER-VAPOR PRESSURE (mb) (WHEN COEXISTENT WITH WATER) | | | | | |
|---|---|---|---|---|---|
| TEMP-ERATURE °C. | 0 | 1 | 2 | 8 | 9 |
| . | . | . | . | . | . |
| . | . | . | . | . | . |
| 0 | 6.1078 | 6.5662 | 7.0547 | 10.722 | 11.474 |
| . | . | . | . | . | . |

TABLE 1-continued

| SATURATED WATER-VAPOR PRESSURE (mb) (WHEN COEXISTENT WITH WATER) | | | | | |
|---|---|---|---|---|---|
| TEMP-ERATURE °C. | 0 | 1 | 2 | 8 | 9 |
| . | . | . | . | . | . |
| 50 | 123.40 | 129.65 | 136.17 | 181.53 | 190.22 |
| . | . | . | . | . | . |
| 90 | 701.13 | 728.19 | 756.11 | 943.02 | 977.61 |

The above-described conventional method of measuring the dew point entails the following problems when dew point measurement is performed in a system, such as a fuel cell power generating system, where a gas with a high dew point exists and where the rated temperature is often above 90° C. The dew point measurement performed can be considerably inaccurate because, as will be clearly understood from Table 1, a change of the dew point by 0.1° C. corresponds to a change of the water vapor partial pressure by about 3%. In such systems, therefore, it is difficult to accurately measure the actual flow rate of steam. In addition, when the measured flow rate of the water vapor is used in a feedback arrangement to achieve the correct flow rate of the steam, a manual operation is performed. As a result, the feedback requires a great amount of labor.

SUMMARY OF THE INVENTION

Accordingly, an object of the present invention is to overcome the above-described problems and provide an apparatus capable of determining, with a high level of precision, the flow rate of steam in a system, such as a fuel cell power generating system, to which a high dew point process gas is supplied, the apparatus being also capable of supplying, with a high level of precision, the correct flow rate of steam to the system.

In an apparatus for measuring the flow rate of steam according to the present invention, an inert gas is mixed with a process gas comprising a first gas (such as natural gas) and steam to obtain a gas mixture. The dew point and the pressure of the gas mixture are measured, and the partial pressure of water vapor in the gas mixture is calculated based on the measured dew point and pressure. Based on the calculated partial pressure and the flow rates of the first gas and the inert gas, the flow rate of water vapor in the process gas is calculated and is used to control the flow rate of steam.

In the apparatus for measuring the flow rate of steam according to the present invention, introducing an inert gas at a known flow rate allows, the partial pressure of the water vapor to be reduced without changing the flow rate of steam so that the dew point at which the partial pressure is measured is lowered. The advantage provided by introducing an inert gas will be understood by considering the case where the process gas has a high dew point of, for instance, above 90° C., and where, as shown in Table 1, a change in the dew point by 0.1° C. corresponds to about 3% change in the partial pressure of the water vapor. According to the present invention, if the dew point at which the water vapor partial pressure is measured is around 50° C., the change in the water vapor partial pressure corresponding to a 0.1° C. change in the dew point is only about 0.5%.

DESCRIPTION OF THE PREFERRED EMBODIMENT

Figure 1:
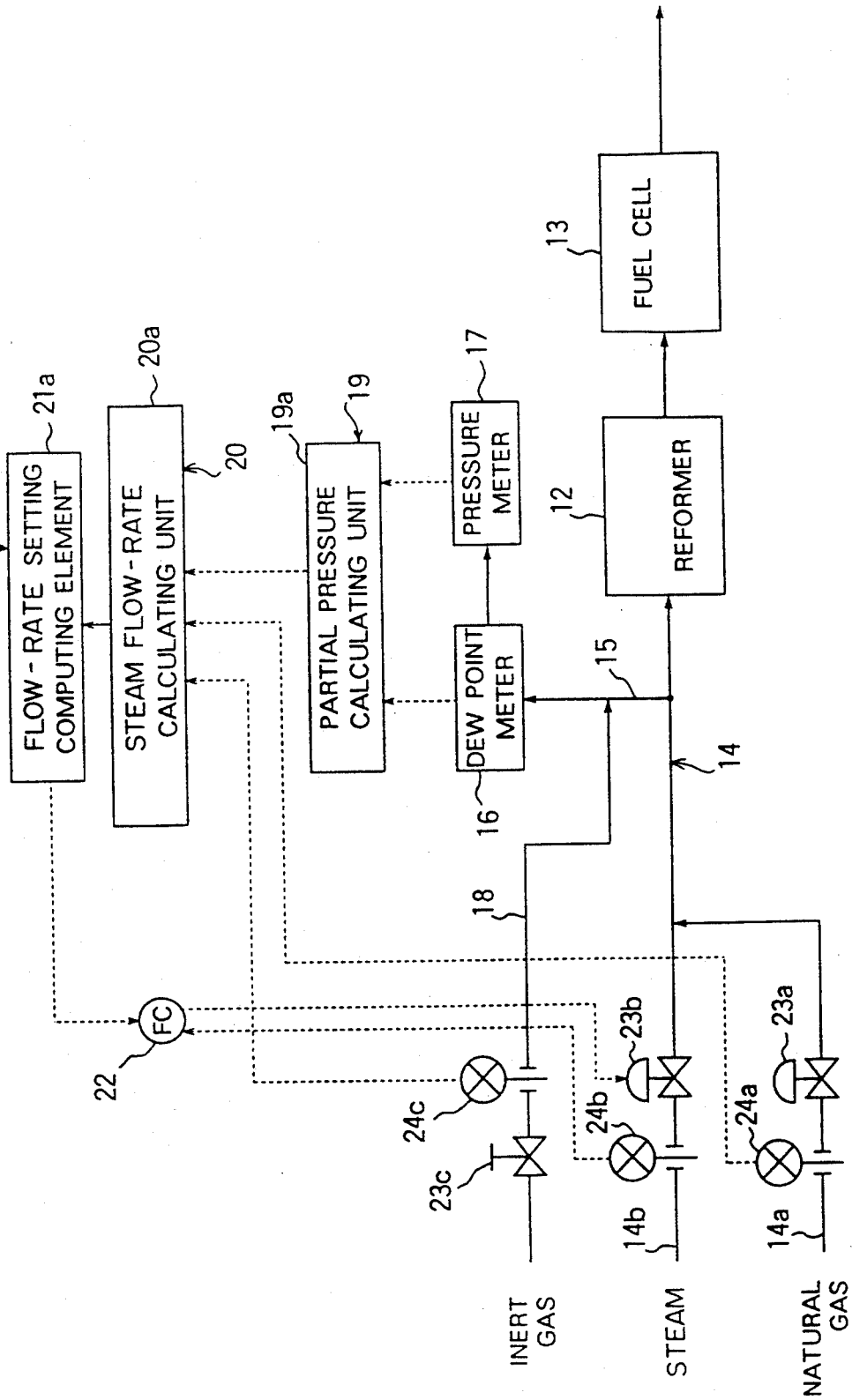
FIG. 1 is a block diagram of an apparatus for measuring the flow rate of steam according to the present invention, the apparatus being incorporated into a fuel cell power generating system.
Figure 2:
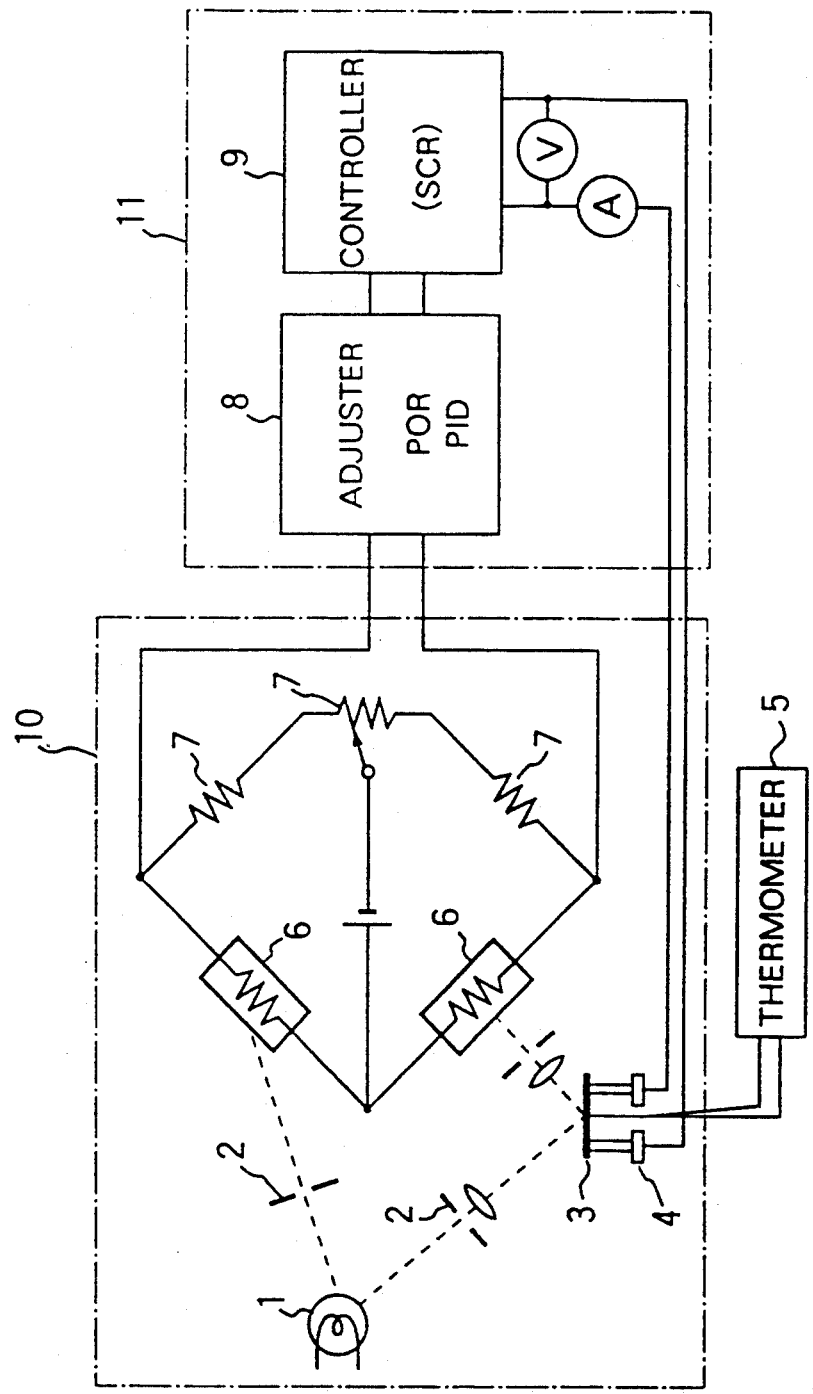
FIG. 2 is a schematic diagram of a thermoelectrically cooled, photoelectric dew point meter.

A preferred embodiment of the present invention will now be described with reference to the drawings. FIG. 1 is a block diagram of a steam flow rate measuring apparatus according to one embodiment of the present invention which is incorporated in a fuel cell power generating system. Referring to FIG. 1, a process gas supply system 14 is connected with a process reactor comprising reformer 12 and fuel cell 13 connected to the reformer 12. The process gas supply system 14 comprises a sub-system 14a for supplying natural gas (not shown) to the reformer 12, and a sub-system 14b for supplying steam (not shown) to the reformer 12. A sample system 15 comprises a dew point meter 16 provided in the vicinity of the entrance of the reformer 12 and a pressure meter 17. The sample system 15 is connected with an inert gas supply means 18 for mixing of an inert gas (nitrogen gas, not shown, in this embodiment) having a known flow rate with the process gas in the sample system 15. A partial pressure calculating means 19 comprising a partial pressure calculating unit 19a calculates the partial pressure of the water vapor contained in a gas mixture of the process gas and the inert gas on the basis of the measurements by the dew point meter 16 and the pressure meter 19. A flow rate calculating means 20 comprising, by a steam flow rate calculating unit 20a calculates the flow rate of the water vapor contained in the process gas on the basis of data including the value calculated by the partial pressure calculating means 19. A correct flow rate setting means 21 comprising a flow rate setting computing element 21a calculates the correct amount of the water vapor flow rate, the actual amount of which has been calculated by the flow rate calculating means 20, and then sets the calculated correct flow rate. A flow controller 22 receives a signal from the correct flow rate setting means 21 which indicates the correct flow rate, and controls the flow rate of steam on the basis of the received signal. The natural gas supply sub-system 14a, the steam supply sub-system 14b and the inert gas supply means 18 include of flow control valves 23a, 23b and 23c, and of flow meters 24a, 24b and 24c, respectively.

Next, the operation of the apparatus will be described.

A certain amount of an inert gas is mixed with the process gas in the sample system 15 provided in the process gas supply system 14 so as to obtain a gas mixture in the sample system 15. The inert gas is supplied at a temperature and flow rate which do not cause the condensation of the water vapor in the sample system 15. The flow rate of the inert gas is set by the inert gas flow meter 24c at a value corresponding to the range within which the dew point meter 16 performs measurement. The dew point of the gas mixture in the sample system 15 is measured by the dew point meter 16 and the pressure of the gas mixture is simultaneously measured by the pressure meter 17. The dew point and the pressure measured by meters 16 and 17, respectively are processed by the partial pressure calculating means 19 so as to obtain the partial pressure of the water vapor contained in the gas mixture.

Next, the flow rate of the inert gas mixed with the process gas in the sample system 15, the flow rate of the natural gas measured by the natural gas flow meter 24a, and the water vapor partial pressure calculated by the partial pressure calculating means 19 are all input to the steam flow rate calculating means 20. In this way, the flow rate of the water vapor is measured at a dew point lower than the dew point which would exist if an inert gas were not mixed with the process gas. Thus, it is possible to accurately control the flow rate of the steam.

The steam flow rate which has thus been obtained is input to the flow rate setting means 21 which sets the correct steam flow rate by causing, through the flow controller 22, the steam flow control valve 24b to generate a feedback signal.

In the above-described embodiment, the system to which a process gas with a high dew-point is supplied is a fuel cell power generating system. However, the present invention may be applied to any system supplied with a high dew point water vapor.

Further, the present invention is not intended to be limited by the arrangement in which an inert gas is mixed with the process gas in the sample system. An inert gas may be mixed directly with the process gas in the process gas system in such a manner that this mixing causes no adverse influence on the entire process.

What is claimed is:

1. An apparatus for measuring the flow rate of water vapor in a process gas including steam comprising:
   first supply means for supplying and measuring the flow rate of a first gas;
   second supply means for supplying steam;
   first mixing means in communication with the first and second supply means for mixing the first gas and the steam to form a process gas;
   third supply means for supplying and measuring the flow rate of an inert gas;
   second mixing means in communication with the first mixing means and the third supply means for mixing the inert gas with the process gas to obtain a gas mixture;
   dew point sensing means in communication with the second mixing means for sensing the dew point of the gas mixture;
   pressure sensing means in communication with the second mixing means for sensing the pressure of the gas mixture at which the dew point was sensed by the dew point sensing means;
   partial pressure calculating means operatively connected to the dew point sensing means and the pressure sensing means for calculating the partial pressure of water vapor in the gas mixture based on the dew point sensed by the dew point sensing means and the pressure sensed by the pressure sensing means; and
   flow rate calculating means operatively connected to the partial pressure calculating means and the first and third supply means for calculating the flow rate of water vapor in the process gas based on the calculated partial pressure, the flow rate of the first gas, and the flow rate of the inert gas.

2. An apparatus as claimed in claim 1 further comprising control means operatively connected to the flow rate calculating means and the second supply means for controlling the flow rate of the steam based on the calculated flow rate.

3. An apparatus as claimed in claim 1 further comprising a reformer connected to the mixing means for receiving the process gas.

4. An apparatus for measuring the flow rate of water vapor in a process gas including steam comprising:
   first supply means for supplying a process gas comprising steam and a first gas;
   sampling means in communication with the first supply means for sampling the process gas to obtain a sample;
   second supply means in communication with the sampling means for supplying an inert gas to the sample to obtain a gas mixture;
   measuring means in communication with the sampling means and downstream of the second supply means for measuring the dew point and the pressure of the gas mixture;
   calculating means operatively connected to the measuring means for calculating the partial pressure of water vapor in the gas mixture based on the measured dew point and pressure;
   determining means for determining the flow rates of the first gas and the inert gas; and
   flow rate calculating means operatively connected to the calculating means and the determining means for calculating the flow rate of water vapor in the process gas based on the calculated partial pressure, the flow rate of the first gas, and the flow rate of the inert gas.

5. An apparatus for measuring the flow rate of water vapor in a mixture including steam comprising:
   mixing means for mixing a first gas at a first known flow rate, an inert gas at a second known flow rate, and steam at an unknown flow rate to obtain a gas mixture;
   supply means for supplying the gas mixture to a process reactor;
   measuring means for measuring the dew point and the pressure of the gas mixture;
   partial pressure calculating means operatively connected to the measuring means for calculating the partial pressure of water vapor in the gas mixture based on the measured dew point and pressure; and
   flow rate calculating means operatively connected to the partial pressure calculating means for calculating the flow rate of water vapor in the steam and the first gas based on the calculated partial pressure, the first known flow rate of the first gas, and the second known flow rate of the inert gas.

6. An apparatus as claimed in claim 5 wherein the supply means supplies the gas mixture to a reformer.

* * * * *